United States Patent [19]

Franko-Filipasic et al.

[11] 4,380,654

[45] Apr. 19, 1983

[54] PROCESS FOR PREPARATION OF 2,3-DIHYDRO-2,2-DIMETHYL-7-HYDROXYBENZOFURAN

[75] Inventors: Borivoj R. Franko-Filipasic, Morrisville, Pa.; Philip B. Hobson, Trenton, N.J.

[73] Assignee: FMC Corporation, Philadelphia, Pa.

[21] Appl. No.: 349,804

[22] Filed: Feb. 18, 1982

[51] Int. Cl.³ .......................................... C07P 307/86
[52] U.S. Cl. ................................................. 549/462
[58] Field of Search ........................................ 549/462

[56] References Cited

U.S. PATENT DOCUMENTS

| | | | |
|---|---|---|---|
| 3,320,286 | 5/1967 | Franko-Filipasic | 260/346.2 |
| 3,356,690 | 12/1967 | Orwoll | 260/346.2 |
| 3,419,579 | 12/1968 | Towns | 260/346.2 |
| 3,474,170 | 10/1969 | Scharpf | 424/285 |
| 3,474,171 | 10/1969 | Scharpf | 424/285 |
| 3,547,955 | 12/1970 | Scharpf | 260/346.2 |
| 4,256,647 | 3/1981 | Michelet et al. | 260/346.2 |
| 4,297,284 | 10/1981 | Michelet | 260/346.22 |
| 4,324,731 | 4/1982 | Michelet et al. | 260/346.22 |

FOREIGN PATENT DOCUMENTS

| | | |
|---|---|---|
| 30511 | 6/1981 | European Pat. Off. |
| 2932458 | 2/1981 | Fed. Rep. of Germany |
| 173437 | 8/1979 | Hungary |

OTHER PUBLICATIONS

Abstract EPC Publication 30511, Corresponding to European Patent 30,511.
Rough Translation and Abstract (CA 91:5106c) of Hungarian 173437.

*Primary Examiner*—John M. Ford
*Assistant Examiner*—Bernard Dentz
*Attorney, Agent, or Firm*—Robert L. Andersen; H. Robinson Ertelt

[57] ABSTRACT

A process for preparing 2,3-dihydro-2,2-dimethyl-7-hydroxybenzofuran in which 2-methallyloxyphenol is heated to a temperature in the range of 150° C. to 250° C. in the presence of a solvent and a Lewis acid catalyst under an autogenous pressure of 20 to 60 psig is disclosed and exemplified.

7 Claims, No Drawings

PROCESS FOR PREPARATION OF 2,3-DIHYDRO-2,2-DIMETHYL-7-HYDROXYBENZOFURAN

The present invention relates to a catechol-based process for preparing 2,3-dihydro-2,2-dimethyl-7-hydroxybenzofuran, an intermediate to the insecticide/nematicide, carbofuran. In particular it relates to a single step process for simultaneously rearranging and cyclizing 2-methallyloxyphenol to 2,3-dihydro-2,2,-dimethyl-7-hydroxybenzofuran at slightly elevated pressure in the presence of a solvent and a Lewis acid catalyst.

In catechol-based processes for preparing 2,3-dihydro-2,2-dimethyl-7-hydroxybenzofuran, catechol is reacted with methallyl chloride to produce 2-methallyloxyphenol (MOP). MOP is subjected to a Claisen rearrangement, and the rearrangement product is cyclized. U.S. Pats. Nos. 3,474,170 and 3,474,171 illustrate this general sequence of reactions and disclose the uncatalyzed rearrangement and cyclization of 2-methallyloxyphenol to 2,3-dihydro-2,2-dimethyl-7-hydroxybenzofuran. The preparatory method described in the foregoing patents is conducted at atmospheric pressures without solvent or catalyst and is an unsatisfactory method for commercially preparing 2,3-dihydro-2,2-dimethyl-7-hydroxybenzofuran.

Various alternative methods for preparation of 2,3-dihydro-2,2-dimethyl-7-hydroxybenzofuran have been explored with a view toward discovery of a more satisfactory and economical process. Several routes have been proposed using analogs of 2-methallyl-oxyphenol which could subsequently be converted to 2,3-dihydro-2,2-dimethyl-7-hydroxybenzofuran. The rearrangement and cyclization of 2-methallyloxynitrobenzene or 2-methallyloxybromobenzene, with and without catalysis, are examples.

Another approach has been for form MOP, place a protective acyl group on the phenolic oxygen of MOP, rearrange and cyclize the resulting 2-acetoxyphenyl methallyl ether, then remove the protective acyl group, a process producing good yields but requiring two extra steps.

In accordance with the present invention it has been found that thermal rearrangement and cyclization of 2-methallyloxyphenol may advantageously be carried out in a single step utilizing a solvent and extremely small quantities of a Lewis acid as a catalyst. The reaction is conducted in a single step, and at relatively low pressure, avoiding the necessity for high pressure equipment. The invention produces high yields of product (selectivity) even when crude 2-methallyloxyphenol is used as a starting material. The invention thus provides a very economical process for producing 2,3-dihydro-2,2-dimethyl-7-hydroxybenzofuran. The overall thermal rearrangement and cyclization may be illustrated as follows:

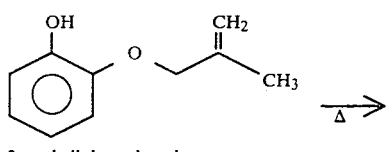
2-methallyloxyphenol

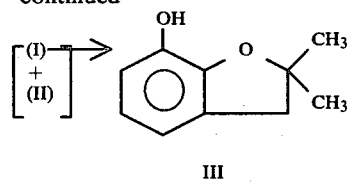

III wherein (I):

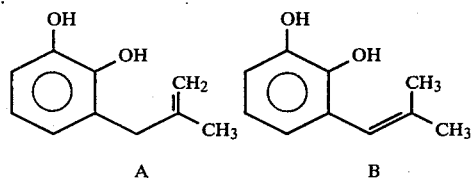

and (II):

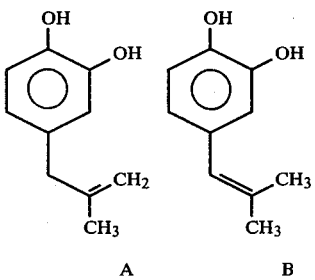

It is well established that the intermediates I and II are formed as a result of a Claisen rearrangement in an approximate ratio of 3:1. It is also established that the intermediates designated IA and IB will cyclize to 2,3-dihydro-2,2-dimethyl-7-hydroxybenzofuran (III), whereas the intermediates designated IIA and IIB will not cyclize to form III. Accordingly, the maximum overall yield that can be expected is about 75–76% due to the inherent limitations in the Claisen rearrangement. In practice, however, it has not been possible to obtain an overall yield of more than about 50–60% by the rearrangement/cyclization of 2-methallyloxyphenol, even when the latter is highly purified.

In the present invention the process is conducted in a single step, without isolation of intermediates or any intermediate treatment, by heating 2-methallyloxyphenol in the presence of a solvent and a catalytic amount of Lewis acid catalyst at a temperature in the range of 150° C. to 250° C. under an autogenous pressure in the range of 20 to 60 psig.

The desired pressures are obtained by heating in a closed or sealed reaction vessel capable of operating at up to about 60 psig. For simplicity such a vessel may be referred to as a pressurizable reactor, with the understanding that the reactor need not be capable of accommodating pressures in excess of those described above. Such pressures are considered for purposes of this invention to be slightly elevated. The reactor is suitable deaerated for use in the presence process.

The best mode known for practicing the invention is to heat 2-methallyloxyphenol in the presence of from about 0.02 to about 0.08 percent by weight aluminum chloride, based on the weight of 2-methallyloxyphenol employed, in the presence of o-xylene or methyl isobutyl ketone as a solvent. More general aspects of the invention will be made apparent in the materials below.

The term Lewis acid, as used herein, means a Lewis acid selected from the group consisting of aluminum chloride, zinc chloride, mercuric chloride, hydrogen chloride, ferrous chloride, rhodium chloride, stannic chloride, magnesium chloride, and ferric chloride. Of these, the best results are obtained with aluminum chloride, zinc chloride, mercuric chloride, and hydrogen chloride; aluminum chloride being preferred.

Prior to the present invention such catalysts have been employed in various cyclization reactions. They have not been used to cyclize Claisen rearrangement products of 2-methallyloxyphenol. Nor have they been present during the Claisen rearrangement. Even when such catalysts were used in prior processes, they were used in substantially larger quantities than are required for the present invention. In the present invention the Lewis acid catalyst is utilized at a level of 0.001 to about 0.2% by weight of the 2-methallyloxyphenol, the preferred range being from about 0.02% to about 0.08%.

Suitable solvents include cyclohexane, isopropanol, various petroleum distillates, ketones such as methyl isobutyl ketone, or aromatic hydrocarbons such as o-xylene. Methyl isobutyl ketone and o-xylene are preferred.

The pressure obtained when conducting this reaction will largely depend on temperature and the particular solvent selected. When methyl isobutyl ketone was used as a solvent at 200° C. pressures of 45 to 70 psig were measured. When o-xylene was used at 200° C., pressures in the range of 20 to 50 psig were obtained.

The reaction may be conducted at any temperature within the range of 150 to 250° C., but a temperature of about 180° C. to 220° C. is preferred. The reaction may be conducted from about 0.5 hours to about 5 hours, but about 2 to about 4 hours is generally preferred.

The following example illustrates the practice of the present invention.

EXAMPLE 1

Synthesis of
2,3-dihydro-2,2-dimethyl-7-hydroxy-benzofuran

A mixture of 12.5 g (95.6% pure, 0.0728 mole) of 2-methallyloxyphenol (MOP) and 0.005 g ($3.7 \times 10^{-5}$ mole) of aluminum chloride in 25.0 of o-xylene was placed in a 110 mll stainless steel autoclave. The autoclave was purged with nitrogen, sealed and heated for 0.5 hour until a temperature of 200° C. was reached. The temperature was held at 200° C. for 3.0 hours, during which the internal pressure was a constant 30 psig. The autoclave was then cooled to room temperature and opened. The reaction mixture was filtered the autoclave rinsed with ethyl acetate and the rinse filtered. The combined filtrates were evaporated under reduced pressure to yield 18.13 of an oil. Analysis of this oil by gas chromatography indicated 50.16% 2,3-dihydro-2,2-dimethyl-7-hydroxybenzofuran, a 76% yield.

Reactions 2 through 52, shown in Table I, illustrate the use of various Lewis acids in o-xylene. The best yields were obtained using aluminum chloride, in many cases equalling or approaching 75–76%. In Table I, unless otherwise noted in the footnotes, all reactions were run in the manner of Example 1. Pressures were in the range of 25–30 psig and the weight ratio of solvent to MOP was about 2.0 to about 2.1.

Reactions 53 through 68, shown in Table II, illustrate the use of various Lewis acids in methyl isobutyl ketone (MIBK). In Table II, unless otherwise noted in the footnote, all reactions were run in the manner of Example 1, pressures were in the range of 45–55 psig and the weight ratio of solvent to MOP was about 2.0 to about 2.1. Reactions 69 through 71 of Table II were run in a sealed glass vessel in cyclohexane as shown in the footnote.

TABLE I

Rearrangement/Cyclization in o-xylene

| Reaction | Catalyst | Amount[a] | Reaction Time (hr) | % Yield[b] |
|---|---|---|---|---|
| 2 | AlCl3 | 0.04 | 2.5 | 70.1 |
| 3 | " | 0.04 | 4.5 | 66.5 |
| 4 | " | 0.02 | 2.5 | 61.0 |
| 5 | " | 0.08 | 3.5 | 69.3 |
| 6 | " | 0.04 | 3.0 | 61.3 |
| 7 | " | 0.04 | 3.5 | 75.4 |
| 8 | " | 0.04 | 3.5 | 50.1 |
| 9 | " | 0.04 | 3.75 | 69.6 |
| 10 | " | 0.04 | 4.25 | 44.9 |
| 11 | " | 0.08 | 3.25 | 68.1 |
| 12 | " | 0.04 | 3.5 | 70.0 |
| 13 | " | 0.04 | 4.5 | 60.0 |
| 14 | ZnCl2 | 0.08 | 2.75 | 59.8 |
| 15 | " | 0.04 | 2.5 | 56.9 |
| 16 | " | 0.08 | 3.5 | 65.8 |
| 17 | " | 0.08 | 4.5 | 65.3 |
| 18[c] | " | 0.08 | 3.0 | 62.3 |
| 19[d] | " | 0.08 | 3.75 | 63.8 |
| 20[e] | " | 0.16 | 4.5 | 61.4 |
| 21 | " | 0.08 | 4.25 | 63.9 |
| 22 | " | 0.08 | 3.0 | 59.4 |
| 23 | " | 0.16 | 3.25 | 55.8 |
| 24 | HgCl2 | 0.4 | 4.0 | 43.7 |
| 25 | " | 0.12 | 3.5 | 65.9 |
| 26 | " | 0.16 | 3.5 | 37.9 |
| 27 | " | 0.12 | 4.0 | 51.0 |
| 28 | " | 0.12 | 4.0 | 50.7 |
| 29 | " | 0.12 | 3.5 | 53.3 |
| 30 | " | 0.2 | 4.5 | 47.5 |
| 31 | " | 0.2 | 3.5 | 37.8 |
| 32 | RhCl3 | 0.08 | 4.75 | 24.0 |
| 33 | " | 0.12 | 4.75 | 23.0 |
| 34 | " | 0.16 | 4.75 | 50.0 |
| 35 | " | 0.2 | 4.5 | 29.3 |
| 36 | " | 0.24 | 4.5 | 47.0 |
| 37 | " | 0.28 | 4.75 | 28.1 |
| 38 | " | 0.32 | 4.5 | 47.2 |
| 39 | " | 0.4 | 4.5 | 30.1 |
| 40 | " | 0.8 | 4.5 | 48.5 |
| 41 | MgCl2 | 0.08 | 4.5 | 25.5 |
| 42 | " | 0.08 | 5.5 | 37.0 |
| 43 | " | 0.08 | 4.5 | 20.9 |
| 44 | " | 0.16 | 4.5 | 37.3 |
| 45 | FeCl2.4H2O | 0.08 | 4.75 | 45.8 |
| 46 | " | 0.16 | 4.75 | 44.6 |
| 47 | SnCl4 | 0.24 | 3.5 | 42.9 |
| 48 | " | 0.64 | 4.5 | 32.2 |
| 49 | HCl | f | 3.5 | 63.6 |
| 50 | " | f | 3.5 | 53.6 |
| 51 | " | f | 2.5 | 52.2 |
| 52 | " | f | 2.5 | 61.8 |

Footnotes:
[a] Weight percent based on weight of 2-methallyloxyphenol starting material.
[b] Gas chromatographic analysis of product.
[c] 40 psig
[d] 55–60 psig
[e] 30–50 psig @ 200–211° C.
[f] Gas bubbled through solvent for 15 minutes

TABLE II

| Reaction | Catalyst | Amount[a] | Reaction Time (hr) | % Yield[b] |
|---|---|---|---|---|
| 53 | AlCl3 | 0.04 | 3.75 | 58.3 |
| 54 | " | 0.08 | 3.75 | 59.2 |
| 55[c] | " | 0.04 | 3.5 | 54.9 |
| 56[d] | " | 0.08 | 3.5 | 38.1 |
| 57[e] | " | 0.04 | 3.5 | 69.2 |
| 58[e] | " | 0.04 | 3.5 | 70.6 |
| 59[e] | " | 0.04 | 4.5 | 71.0 |
| 60[e] | " | 0.04 | 4.0 | 70.3 |
| 61 | ZnCl2 | 0.08 | 3.0 | 52.3 |
| 62 | " | 0.08 | 4.5 | 56.7 |
| 63 | " | 0.08 | 3.0 | 58.0 |

TABLE II-continued

| Reaction | Catalyst | Amount[a] | Reaction Time (hr) | % Yield[b] |
|---|---|---|---|---|
| 64 | " | 0.08 | 3.0 | 58.6 |
| 65 | " | 0.16 | 2.5 | 60.5 |
| 66 | " | 0.16 | 3.5 | 59.2 |
| 67[f] | " | 0.16 | 3.5 | 42.5 |
| 68[g] | " | 4.0 | 4.5 | 27.8 |
| 69[h] | $RhCl_3$ | 0.25 | — | 73 |
| 70[h] | $RhCl_3$ | 0.02 | 2.25 | 44 |
| 71[h] | $AlCl_3$ | 0.001 | 2.0 | 68.0 |

Footnotes:
[a] Weight percent based on weight of 2-methallyloxyphenol.
[b] Gas chromatographic analysis of product.
[c] Ratio Solvent/MOP = 2.5, 65 psig
[d] Ratio Solvent/MOP = 3.4, 60–70 psig
[e] Ratio Solvent/MOP = 0.5
[f] 60 psig
[g] 60–65 psig
[h] Solvent/MOP Ratio = 1, Run in sealed glass vial at 200° C. in cyclohexane; pressure not measured.

We claim:

1. A process for thermally rearranging and cyclizing 2-methallyloxyphenol in the presence of a solvent to form 2,3-dihydro-2,2-dimethyl-7-hydroxybenzofuran which comprises heating 2-methallyloxyphenol in a pressurizable reactor at a temperature in the range of 150° C.–250° C. in the presence of a catalytic amount of Lewis acid catalyst selected from the group consisting of aluminum chloride, zinc chloride, mercuric chloride, hydrogen chloride, ferrous chloride, rhodium chloride, stannic chloride, magnesium chloride and ferric chloride, under an autogenous pressure in the range of 20 to 60 psig.

2. The process of claim 1 in which said reaction is conducted in the presence of a solvent producing an autogenous pressure in the range of 25 to 50 psig at 200° C.

3. The process of claim 2 in which said Lewis acid is selected from the group consisting of aluminum chloride, zinc chloride, mercuric chloride, and hydrogen chloride, said solvent being selected from the group consisting of o-xylene, methyl isobutyl ketone, and cyclohexane.

4. The process of claim 3, catalyzed with aluminum chloride, in the presence of o-xylene at a temperature in the range of 180° C. to 220° C. under an autogenous pressure of 25 to 35 psig.

5. The process of claim 4 in which there is employed from 0.02 to about 0.08 weight percent of aluminum chloride based on 2-methallyloxyphenol.

6. The process of claim 3 catalyzed with aluminum chloride in the presence of methyl isobutyl ketone at a temperature in the range of 180° C. to 220° C. under an autogenous pressure of 40 to 60 psig.

7. The process of claim 1, 2, 3, 4, 5 or 6 in which the desired operating temperature is maintained for from 2.5 to about 4.5 hours.

* * * * *